United States Patent
Lozman et al.

(10) Patent No.: US 8,821,392 B2
(45) Date of Patent: *Sep. 2, 2014

(54) SURGICAL RETENTION PORT AND METHOD OF USE

(75) Inventors: Philip R. Lozman, Miami, FL (US); Scott L. Jahrmarkt, Miami Beach, FL (US); Jerry S. Sher, Bal Harbour, FL (US); Jeremy Louis Hemingway, Cincinnati, OH (US); David Charles Perdue, Cincinnati, OH (US); Paul J. Grata, Hialeah, FL (US)

(73) Assignee: Joint Product Solutions, LLC, Miami Beach, FL (US)

(*) Notice: Subject to any disclaimer, the term of this patent is extended or adjusted under 35 U.S.C. 154(b) by 204 days.

This patent is subject to a terminal disclaimer.

(21) Appl. No.: 13/203,062

(22) PCT Filed: Jan. 19, 2010

(86) PCT No.: PCT/US2010/021339
§ 371 (c)(1),
(2), (4) Date: Aug. 24, 2011

(87) PCT Pub. No.: WO2010/098905
PCT Pub. Date: Sep. 2, 2010

(65) Prior Publication Data
US 2011/0306841 A1   Dec. 15, 2011

Related U.S. Application Data

(60) Provisional application No. 61/155,318, filed on Feb. 25, 2009.

(51) Int. Cl.
A61B 1/32   (2006.01)

(52) U.S. Cl.
USPC .......................................................... 600/204

(58) Field of Classification Search
USPC .............................. 600/204; 604/164.03, 177
See application file for complete search history.

(56) References Cited

U.S. PATENT DOCUMENTS

| | | | |
|---|---|---|---|
| 3,039,468 A * | 6/1962 | Price | 604/540 |
| 3,397,699 A | 8/1968 | Kohl | |
| 3,717,151 A | 2/1973 | Collett | |
| 4,393,873 A | 7/1983 | Nawash et al. | |
| 5,002,557 A | 3/1991 | Hasson | |
| 5,073,166 A | 12/1991 | Parks et al. | |
| 5,104,383 A | 4/1992 | Shichman | |
| 5,122,122 A | 6/1992 | Allgood | |
| 5,129,885 A | 7/1992 | Green et al. | |
| 5,147,316 A | 9/1992 | Castillenti | |
| 5,176,697 A | 1/1993 | Hasson et al. | |
| 5,203,773 A | 4/1993 | Green | |

(Continued)

*Primary Examiner* — Nicholas Woodall
(74) *Attorney, Agent, or Firm* — Gordon & Jacobson, PC

(57) ABSTRACT

A surgical retention port particularly useful as an arthroscopic port for shoulder surgery is provided. The surgical retention port has a long pointed instrument such as a trocar or obturator, an inner cannula extending around the pointed instrument, a plurality of rotatable fingers coupled to the inner cannula, and an outer cannula extending around the inner cannula. In one embodiment of the invention, the inner cannula and long pointed instrument are keyed such that rotation of the long pointed instrument can effect rotational movement of the inner cannula. Rotation of the inner cannula in turn causes the rotation of the fingers from a first position where the fingers assume a collapsed configuration to a second position where the fingers assume an extended or open configuration.

38 Claims, 6 Drawing Sheets

(56) References Cited

U.S. PATENT DOCUMENTS

| | | |
|---|---|---|
| 5,217,451 A | 6/1993 | Freitas |
| 5,232,451 A | 8/1993 | Freitas et al. |
| 5,248,302 A | 9/1993 | Patrick et al. |
| 5,273,529 A | 12/1993 | Idowu |
| 5,330,497 A | 7/1994 | Freitas et al. |
| 5,336,176 A | 8/1994 | Yoon |
| 5,423,770 A | 6/1995 | Yoon |
| 5,429,598 A | 7/1995 | Waxman et al. |
| 5,445,615 A | 8/1995 | Yoon |
| 5,549,595 A | 8/1996 | Freitas |
| 5,637,097 A | 6/1997 | Yoon |
| 5,653,718 A | 8/1997 | Yoon |
| 5,688,247 A | 11/1997 | Haindl et al. |
| 5,707,362 A | 1/1998 | Yoon |
| 5,713,870 A | 2/1998 | Yoon |
| 5,741,234 A | 4/1998 | Aboul-Hosn |
| 5,746,720 A | 5/1998 | Stouder, Jr. |
| 5,782,813 A | 7/1998 | Yoon |
| 5,817,062 A | 10/1998 | Flom et al. |
| 5,830,125 A | 11/1998 | Scribner et al. |
| 5,836,913 A | 11/1998 | Orth et al. |
| 5,857,999 A | 1/1999 | Quick et al. |
| 5,871,471 A | 2/1999 | Ryan et al. |
| 5,882,340 A | 3/1999 | Yoon |
| 5,935,107 A | 8/1999 | Taylor et al. |
| 5,971,960 A * | 10/1999 | Flom et al. ............ 604/174 |
| 5,989,225 A | 11/1999 | Bodicky et al. |
| 6,162,236 A | 12/2000 | Osada |
| 6,197,002 B1 | 3/2001 | Peterson |
| 6,423,034 B2 | 7/2002 | Scarfone et al. |
| 6,423,036 B1 | 7/2002 | Van Huizen |
| 6,451,041 B1 | 9/2002 | Moenning et al. |
| 6,451,042 B1 * | 9/2002 | Bonutti ............ 606/190 |
| 6,565,536 B1 | 5/2003 | Sohn |
| 6,589,214 B2 | 7/2003 | McGuckin, Jr. et al. |
| 6,632,197 B2 | 10/2003 | Lyon |
| 6,676,639 B1 | 1/2004 | Ternstrom |
| 6,743,207 B2 | 6/2004 | Elbert et al. |
| 6,764,464 B2 | 7/2004 | McGuckin, Jr. et al. |
| 6,770,053 B2 | 8/2004 | Scarfone et al. |
| 6,884,235 B2 | 4/2005 | McGuckin, Jr. et al. |
| 6,925,320 B2 | 8/2005 | Gruhl |
| 6,929,621 B2 | 8/2005 | Whitmore, III et al. |
| 6,972,026 B1 | 12/2005 | Caldwell et al. |
| 7,186,238 B2 | 3/2007 | Elbert et al. |
| 8,409,085 B2 * | 4/2013 | Lozman et al. ............ 600/204 |
| 2003/0158519 A1 | 8/2003 | Epstein et al. |
| 2004/0154623 A1 | 8/2004 | Schaeffer et al. |
| 2005/0251196 A1 | 11/2005 | Wong |
| 2006/0142697 A1 | 6/2006 | Hawk et al. |
| 2008/0041391 A1 | 2/2008 | Worley |
| 2008/0125756 A1 | 5/2008 | DiCarlo et al. |
| 2011/0082339 A1 * | 4/2011 | Elliott, III ............ 600/204 |

* cited by examiner

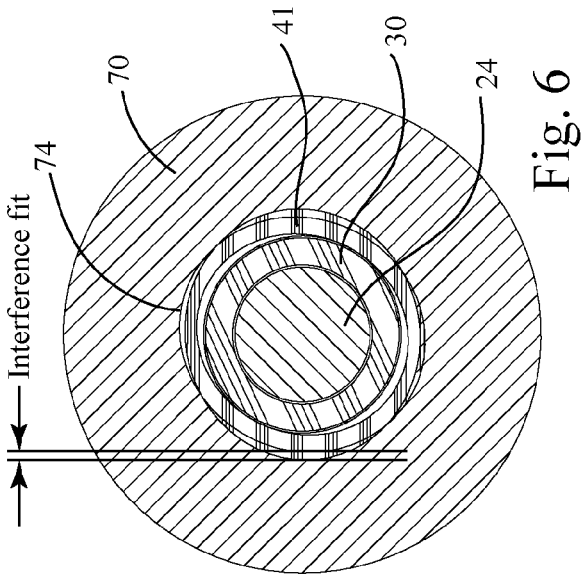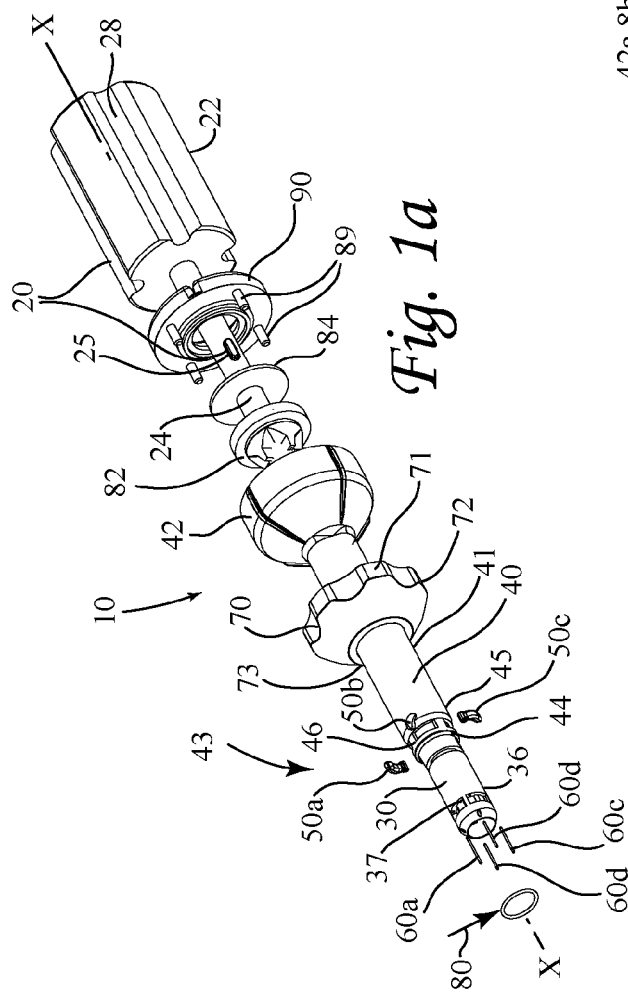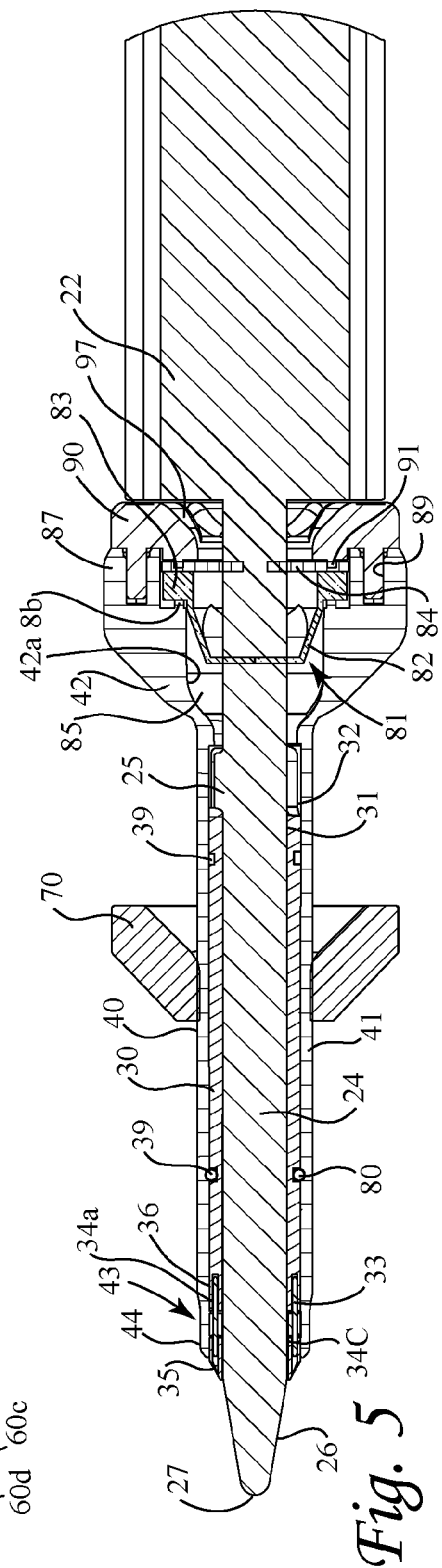

Closed

Open

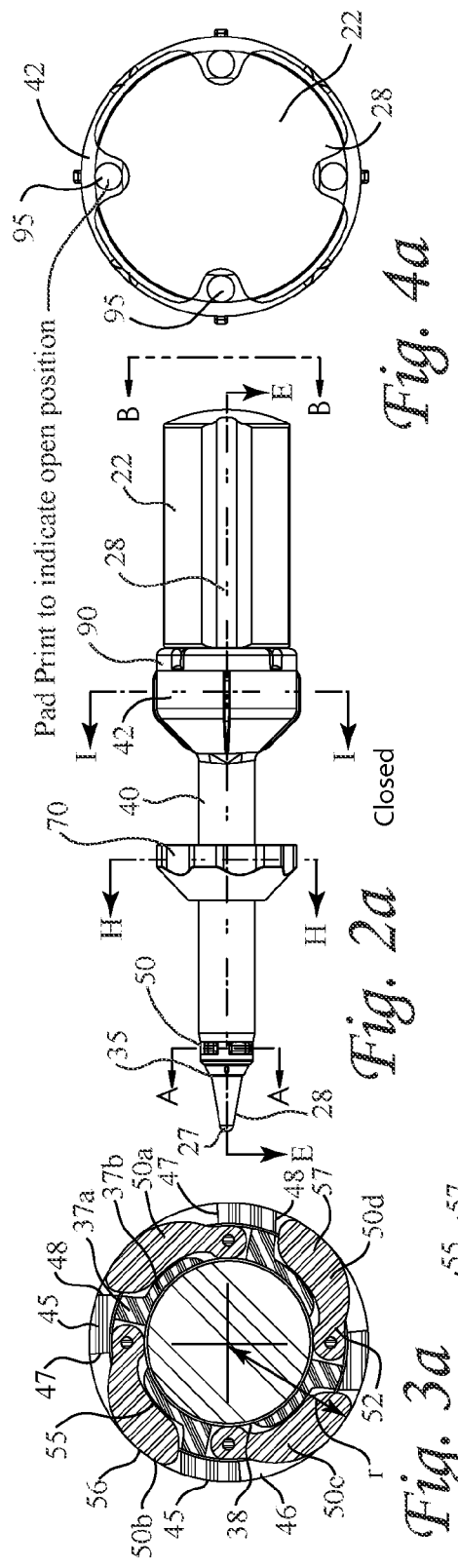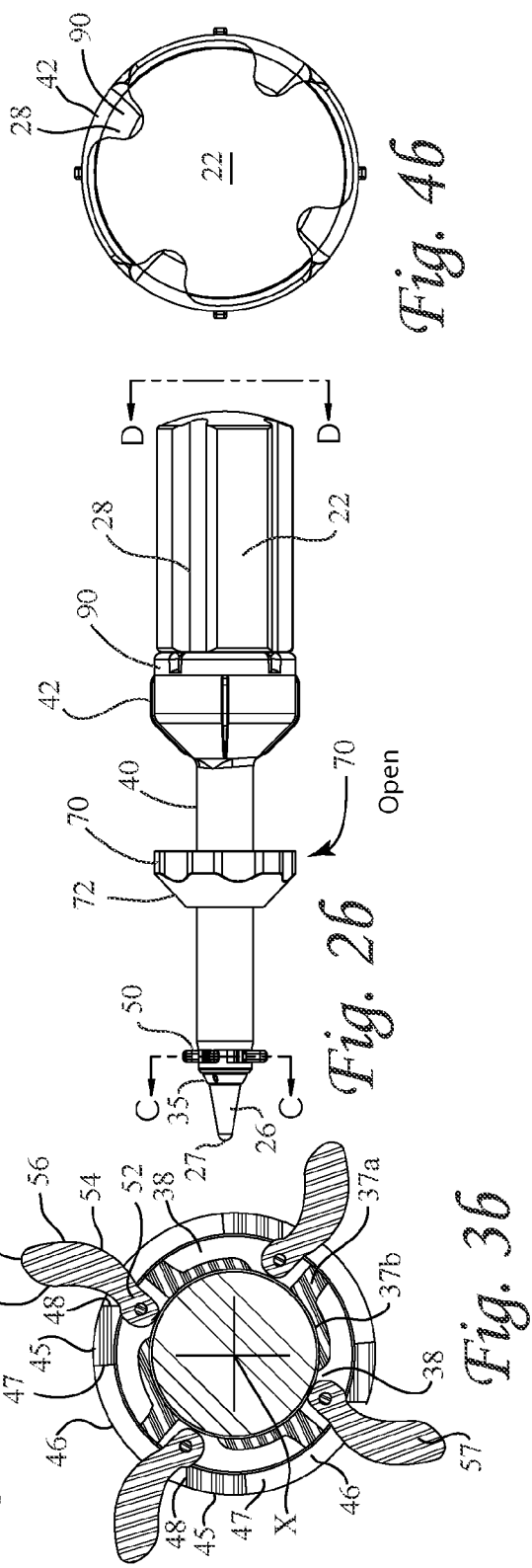

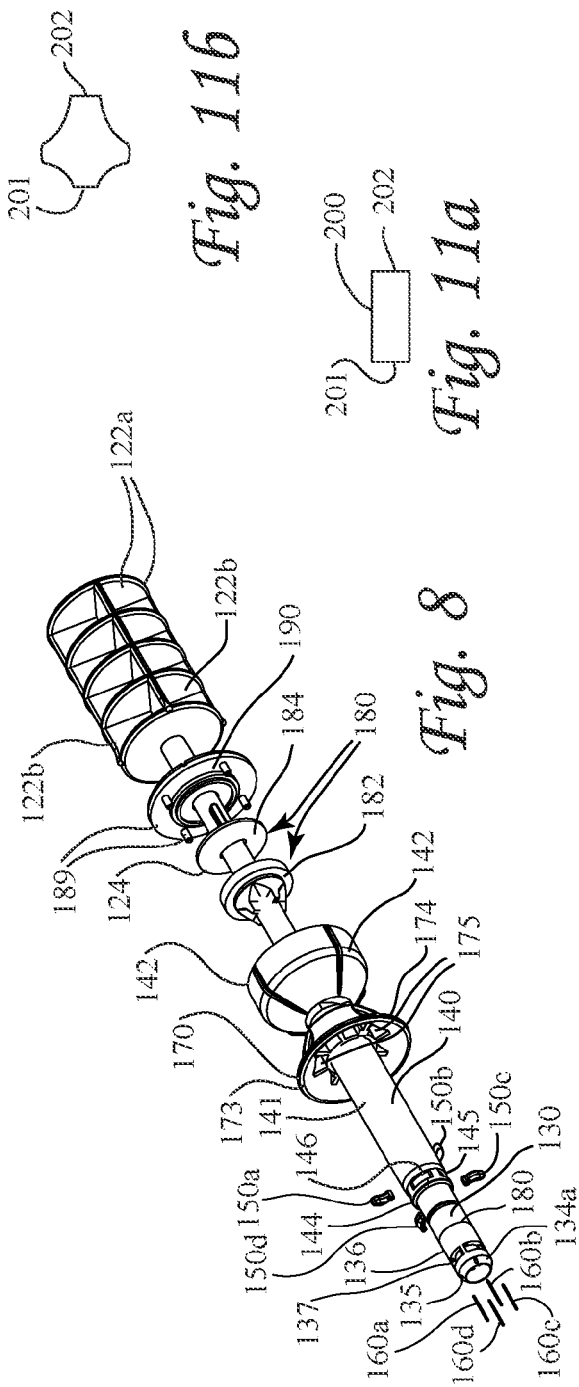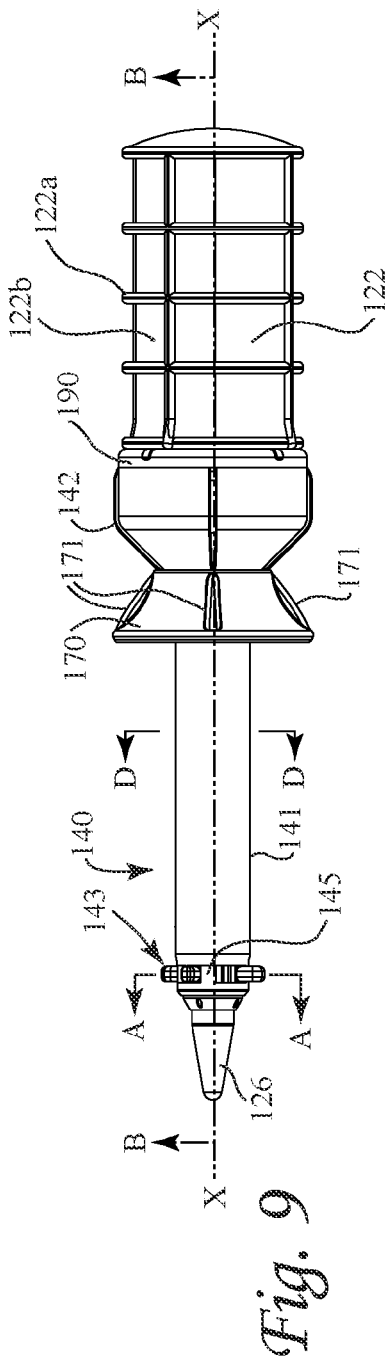

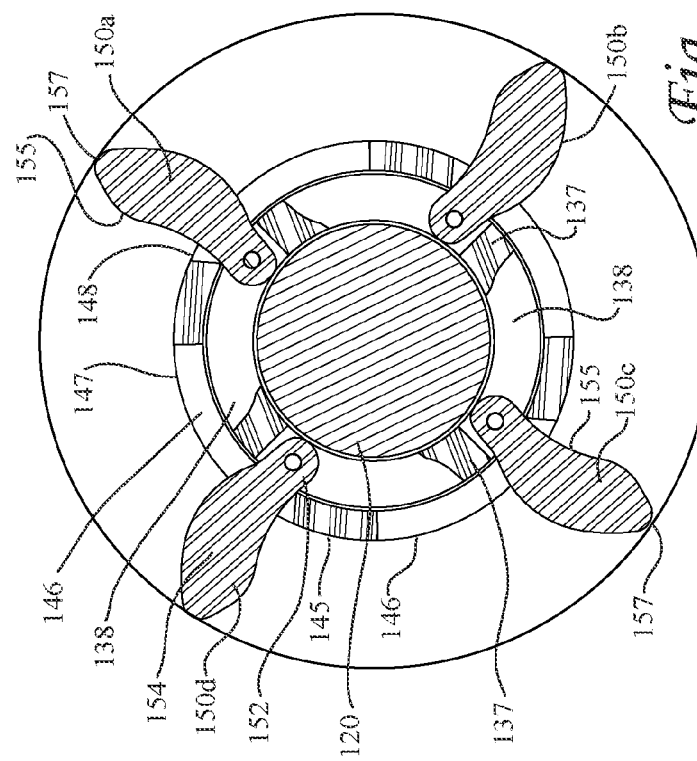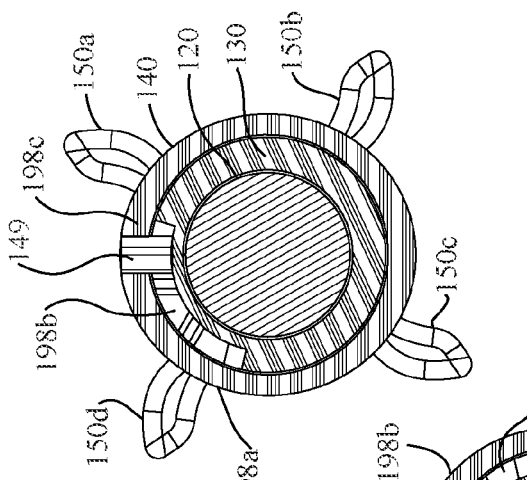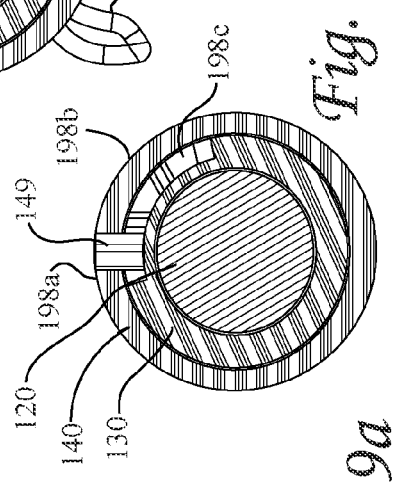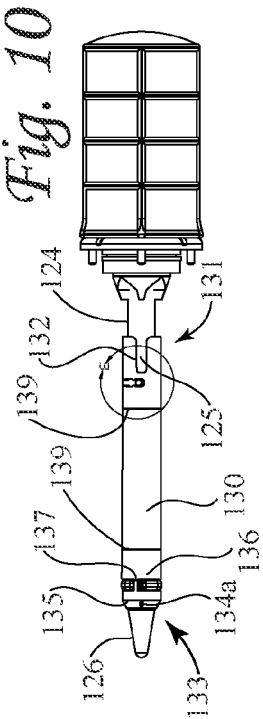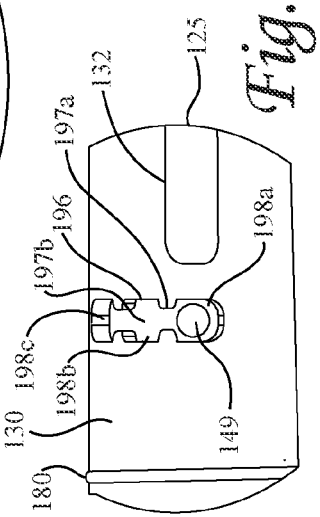

SURGICAL RETENTION PORT AND METHOD OF USE

CROSS-REFERENCE TO RELATED APPLICATIONS

This application is a 371 national stage entry claiming priority from PCT application no. PCT/US10/21339, with an international filing date of Jan. 19, 2010, which claims benefit from U.S. provisional application Ser. No. 61/155,318, filed Feb. 25, 2009.

BACKGROUND OF THE INVENTION

1. Field of the Invention

This invention relates broadly to surgical instruments and methods. More particularly, this invention relates to a surgical retention port and its method of use and is particularly suited for arthroscopic surgery and even more particularly suited for arthroscopic shoulder surgery, although it is not limited thereto.

2. State of the Art

Arthroscopy is a minimally invasive surgical procedure used to survey or repair the interior of a joint or surrounding structures. Arthroscopy is conducted by inserting an arthroscope (endoscope) into the joint through a small incision and one or more arthroscopic tools through one or more additional incisions. Irrigation fluid is pumped into the joint in order to distend the joint. Often, a trocar port device is used to make or dilate the incision and provide a port. The trocar port typically includes a pointed instrument (trocar or obturator) and a cannula (port) extending around the trocar or obturator. The trocar or obturator is used to incise and/or expand an incision so that the cannula can be pushed into the incision. Then, the trocar or obturator can be removed from the cannula with the cannula remaining in the incision and acting as a port through which an arthroscopic instrument can be inserted. The cannula of the trocar port device is often provided with a valve to prevent the escape of irrigation fluid from the surgical space.

In order to minimize trauma, sometimes it is desirable to anchor the cannula in place in the incision. In these situations it is known to provide a retaining mechanism on the cannula. Examples of such retaining mechanisms in various laparoscopic arts include U.S. Pat. No. 3,397,699 to Kohl (relating to a retaining catheter), U.S. Pat. No. 5,002,557 to Hasson (relating to a retaining cannula utilizing a balloon), U.S. Pat. No. 5,203,773 to Green (relating to a tissue gripper for use with a cannula), U.S. Pat. No. 6,589,214 to McGuckin, Jr. et al. (relating to a vascular introducer sheath with a retainer). Unfortunately, none of the retaining cannulae known in the art have been particularly effective with respect to arthroscopic surgery. The joint space is relatively small when compared to other larger body cavites such as the thoracic or abdominal cavity. The field of view is thus relatively small and can be further compromised by surrounding bony, tendinous, ligamentous and synovial anatomic structures. These structures with an already limited field of view can further confound effective deployment of known or existing retaining cannulae.

SUMMARY OF THE INVENTION

The present invention provides a surgical retention port. According to one aspect of the invention, the surgical retention port is particularly useful as an arthroscopic port for shoulder surgery.

According to another aspect of the invention, the surgical retention port has a long pointed instrument such as a trocar or obturator, an inner cannula extending around the pointed instrument, a plurality of rotatable fingers coupled to the inner cannula, and an outer cannula extending around the inner cannula. According to one embodiment of the invention, the inner cannula and long pointed instrument are keyed such that rotation of the long pointed instrument can effect rotational movement of the inner cannula. Rotation of the inner cannula in turn causes the rotation of the fingers from a first position where the fingers assume a collapsed configuration to a second position where the fingers assume an extended or open configuration.

According to one embodiment of the invention, the pointed instrument includes a shaft, a distal tip capable of dilating an incision, a proximal handle, and a mechanism for engaging with the inner cannula so that rotation of the pointed instrument can result in rotation of the inner cannula. The pointed instrument is longitudinally movable relative to the inner cannula and can be withdrawn completely from the inner and outer cannulas. The inner cannula includes a mechanism for engaging with the mechanism of the pointed instrument. The rotatable fingers are coupled to the inner cannula at a distal end thereof and can rotate about pivots on the inner cannula. The hollow outer cannula has a handle at its proximal end including a seal, and a distal end having a plurality of windows with a plurality of longitudinally extending bars between the windows. In a collapsed configuration, the rotatable fingers assume a collapsed arrangement so that they are contained within the plurality of windows and preferably within a periphery of the outer cannula. In an extended or open configuration, the fingers rotate and extend radially through the windows and beyond the periphery of the outer cannula in a manner substantially perpendicular to the longitudinal axis of the port.

Objects and advantages of the invention will become apparent to those skilled in the art upon reference to the detailed description taken in conjunction with the provided figures.

BRIEF DESCRIPTION OF THE DRAWINGS

FIG. 1a is an exploded perspective view of a first embodiment of a surgical retention port.

FIG. 2a is a side view of the surgical retention port of FIG. 1a in a closed position.

FIG. 2b is a side view of the surgical retention port of FIG. 1a in an open position.

FIG. 3a is a cross-sectional view along line A-A of FIG. 2a.

FIG. 3b is a cross-sectional view along line C-C of FIG. 2b.

FIG. 4a is a rear view of the surgical retention port of FIG. 1a in the closed position seen from line B-B of FIG. 2a.

FIG. 4b is a rear view of the surgical retention port of FIG. 1a in the open position seen from line D-D of FIG. 2b.

FIG. 5 is a cross sectional view along line E-E of FIG. 2a.

FIG. 6 is a cross-sectional view along line H-H of FIG. 2a.

FIG. 7 is a cross-sectional view along line I-I of FIG. 2a.

FIG. 8 is an exploded perspective view of a second embodiment of a surgical retention port.

FIG. 9 is a side view of the second embodiment of FIG. 8 in an open position.

FIG. 9a is a cross sectional along line A-A of FIG. 9.

FIG. 9b is a view taken along line D-D of FIG. 9.

FIG. 9c is a similar view of FIG. 9b but with the fingers of the surgical retention port in an open position.

FIG. 10 is a side view of the obturator and inner cannula of the second embodiment and without the outer cannula except for a portion of the pin of the outer cannula.

FIG. 10a is an enlarged view of a locking slot area of the inner cannula of the second embodiment.

FIG. 11a is a side view of an elastomeric sleeve which may be used in conjunction with the first and second embodiments of the surgical retention port.

FIG. 11b is a side view of the elastomeric sleeve of FIG. 11a shown in a tenting position.

DETAILED DESCRIPTION OF THE PREFERRED EMBODIMENTS

Figure 1B:
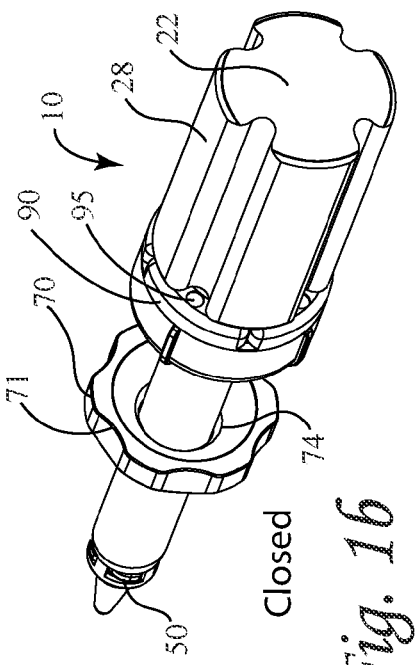
FIG. 1b is a rear perspective view of the surgical retention port of FIG. 1a in a closed position.

Turning now to FIGS. 1a-1d, a first presently preferred embodiment of a surgical retention port of the invention is seen. The surgical retention port 10 of FIGS. 1a-1d broadly includes a long pointed instrument (trocar or obturator) assembly 20, an inner cannula 30, an outer cannula assembly 40, rotatable fingers 50a-50d (three shown in FIG. 1a) which are coupled by pins 60a-60d to the inner cannula 30, and an optional locking collar 70. At least one o-ring 80 is preferably provided as will be described hereinafter.

As seen in FIGS. 1a and 5, the long pointed instrument assembly 20 includes a proximal handle 22, a shaft 24 defining a longitudinal axis x and having a rib, key or other interface mechanism 25 for rotating the inner cannula 30 (as described in more detail hereinafter), and a pointed distal tip 26 which is preferably capable of dilating an incision. In the first embodiment, the pointed instrument assembly is an obturator assembly as the pointed tip includes a rounded end 27 does not have any sharp edges. However, if desired, the pointed tip could have sharp edges and function as a trocar. As seen in FIGS. 1a-1d, 2a, 2b, 4a and 4b, the proximal handle 22 has longitudinal cut-outs or grooves 28 which aid in gripping the handle as well as helping to provide a mechanism for determining whether the port 10 is in an open or closed position (as will be described in more detail hereinafter).

As seen in FIGS. 1a and 5, the hollow inner cannula 30 extends about the long pointed instrument 20 in a manner which permits the long pointed instrument 20 to be movable longitudinally relative to said inner cannula 30. Thus, by gripping the handle 22 and moving it distally and proximally, the shaft 24 of the long pointed instrument 20 can be inserted into and through the cannula 30 and can be removed completely from the inner cannula 30. The inner cannula 30 has at its proximal end 31 at least one groove, slot or keyway (i.e., a second interface mechanism) 32 which is designed to receive the rib or key interface 25 of the shaft 24 of the long pointed instrument 20. In the preferred embodiment, four such keyways are provided at ninety degree rotations about the proximal end 31 of the inner cannula 30. When the rib or key of shaft 24 is engaged in a keyway 32 of the inner cannula, rotation of the long pointed instrument 20 about the long axis x causes rotation of the hollow inner cannula 30. In addition, the inner cannula 30 has a distal end 33 which defines four longitudinal holes 34a-34d (two shown in FIG. 5) which receive pins 60a-60d. As will be described in more detail hereinafter, and as seen in FIGS. 1a, 3a, 3b and 5, the very distal end of said hollow inner cannula comprises a tapered distal ring 35 coupled to a more proximal portion 36 of the distal end 33 of the hollow inner cannula 30 by a plurality of links 37. In the first embodiment, the links 37 each have a first portion 37a having a thickness substantially equal to the thickness of the hollow inner cannula 30 and a second radially extending portion 37b having a thickness less than the thickness of the hollow inner cannula 30. The radially extending portions 37b prevent the distal ends of hooked instruments which may be inserted into the port from getting caught in the distal end of the inner cannula 30. The links 37 define a plurality of gaps 38 in which at least a portion of the fingers 50 are located, as will be described in more detail hereinafter. The pins 60a-60d extend from the longitudinal holes 34a-34d in the distal ring 35 through the gaps 38 (and fingers 50) and into the holes 34a-34d in the more proximal portion 36 of the distal end of cannula 30. Proximal of the distal end 33 of the inner cannula 30 and distal the proximal end 31, the inner cannula 30 has at least one groove 39 (two shown in FIG. 5) in its outer surface for receiving an o-ring 80. The o-ring(s) seat(s) in the groove 39 and serve(s) the dual functions of providing friction to rotational movement of the inner cannula 30 relative to the outer cannula 40, and preventing fluid from exiting the surgical site through any gaps between the cannulas. The groove 39 may be circular, or, as described hereinafter with respect to the embodiment of FIGS. 12a and 12b may be oval to serve a locking function.

Details of the outer cannula 40 are best seen in FIGS. 1a, 3a, 3b, and 5. The outer cannula 40 includes an elongate portion 41, a proximal end 42 which houses a valve assembly 81 (discussed in more detail hereinafter), and a distal end 43. At least a part of the elongate portion 41 of the cannula preferably has a slightly oval cross-section as described hereinafter with reference to FIG. 6. In fact, as described hereinafter with respect to the embodiment of FIGS. 12a and 12b, both the inner and outer surfaces of outer cannula 40 may include portions which are oval. The distal end 43 of the outer cannula 40 includes a tapered ring 44 coupled to the remainder of the distal end by a plurality of longitudinal bars 45 which define windows 46. The bars have two lateral faces 47, 48 which act as camming surfaces for the fingers 50 such that rotation of the inner cannula 30 in a first rotational direction relative to said outer cannula 40 causes the fingers to engage one face (e.g., 47), and rotation of the inner cannula in the opposite direction causes the fingers to engage the other face (e.g., 48), as described in more detail below.

As previously mentioned, fingers 50a-50d are coupled to the inner cannula 30 by pins 60a-60d. As seen best in FIGS. 3a and 3b, each of the fingers 50a-50d has an integral pivot portion 52 which rotates about the pins and an extending portion 54 which extends radially outwardly in an "open" position (FIG. 3b). More particularly, in cross-section, each finger 50 takes the general form of a shoe footprint with the heel being the pivot portion 52, and the sole being the extending portion 54. As seen in FIGS. 3a and 3b, the pivot portions 52 sit in the gap areas 38 of the distal end of the inner cannula 30, and the pivot portions 52 have a thickness or diameter substantially equal to the diameter of the inner cannula 30. Also, as seen in FIG. 3a, in a closed or collapsed configuration, the extending portions 54 of the feet sit in the gap areas 38 of the inner cannula 30 as well as in the windows 46 of the outer cannula 40. In the collapsed configuration, the inside surface 55 of the extending portions 54 of the fingers engages or is adjacent the radially extending portions 37b of the links 37 of the distal end of the inner cannula 30, while an outside surface 56 is substantially within the periphery (outer surface) of the outer cannula 40. In a preferred embodiment, a portion of the outside surface 56 is defined by a radius r equal to the radius of the outer surface of the outer cannula 40. In a second open or extended configuration seen in FIG. 3b, the extending portions 54 of the fingers 50 extend radially through the windows 46 in the outer cannula 40 and well beyond the periphery in a manner substantially perpendicular to the longitudinal axis x of the pointed instrument 20. In a preferred embodiment, the diameter of the instrument 10 defined by the open fingers from tip 57 to tip 57 is approximately sixty percent larger than the diameter of the distal portion 43 of the outer cannula 40. The fingers 50 are constructed to be substantially small in radial dimension when in the open configuration, yet sufficiently large and stiff to support the cannula. The curvilinear shape of the fingers is adapted to keep the fingers confined to the cannula when in the closed configuration, yet have a surface area that would minimize trauma to the tissue when in the open configuration. In a preferred embodiment the fingers are 0.25 inch in radial dimension and 0.10 inch in longitudinal thickness (a 5 to 2 ratio of radial dimension to longitudinal thickness dimension) which provides the desired properties given the materials and shapes of the fingers.

With the inner cannula 30, outer cannula 40, and fingers 50 arranged as described, it will be appreciated that with the fingers 50 in a collapsed configuration as in FIG. 3a, upon rotation of the inner cannula 40 counterclockwise (looking distally), the inside surfaces 55 of the fingers 50 near their tips 57 will engage the camming surfaces or faces 48 of first bars 45 of the outer cannula 40 such that the faces 48 will force the fingers 50 to rotate about the pins 60 and extend radially outerwardly. Eventually, after about sixty to sixty-five degrees of counterclockwise rotation, and as suggested by FIG. 3b, the outside surfaces of the rotating portions 52 will engage an outer edge of the thick portions 37a of the links 37 such that rotation cannot continue. In the opposite direction, from the fully open position of FIG. 3b, rotation of the inner cannula 40 in a clockwise direction (looking distally) will not cause the fingers 50 to start closing until the outer surfaces 56 of the extending portions 54 of the fingers are engaged by the camming surfaces 47 of second bars 45 (which occurs after about fifty degrees of clockwise rotation from the fully open position). Continued clockwise rotation eventually causes the complete closing of the fingers 50 as shown in FIG. 3a. Thus, for any given finger, one bar 45 of the outer cannula 40 causes the finger to open, while a second bar 45 which is located ninety degrees clockwise of the first bar causes the finger to close.

As previously described, rotation of the inner cannula 30 relative to the outer cannula 40 is obtained by rotation of the elongate pointed instrument 20 relative to the outer cannula 40. In particular, as previously described, the rotation of instrument 20 causes engagement of a projection, rib, or key 25 on the instrument 20 with a groove, slot, or keyway in the inner cannula 30. The rotation is typically accomplished by a practitioner through gripping the handle 22 of the instrument 20 in one hand, and the proximal end 42 of the outer cannula 40 with the other hand and rotating one or the other.

Figure 7:
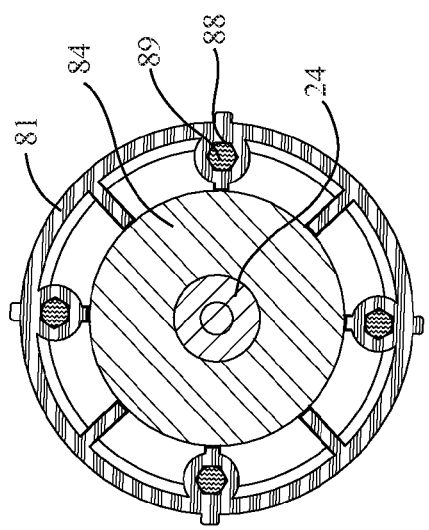

Details of the proximal end 42 of the outer cannula 40 are seen in FIG. 5. As previously mentioned, the proximal end 42 provides a housing for a valve assembly 81 which includes a polymeric flexible cross slit valve 82 having a base 83 and a polymeric stretchable washer valve 84 which engages the proximal side of the base 83 of the slit valve 82. The housing has an inner surface 42a which defines an enlarged cavity 85 in which the valves 82 and 83 are located. Extending proximally from the housing is an inner circumferential projection 86 as well as a proximal arm 87 which defines a plurality of holes 88 configured for receiving pins 89 of an end cap 90. As seen in FIG. 5, the circumferential projection 86 engages the proximal side of the base 83 of the slit valve 82. The distal side of the washer valve 84 is engaged by a projection 91 on the end cap 90. In this manner, the washer valve 84 and slit valve 82 are held in place in the cavity 85 of the housing of the outer cannula 40 when the pins 89 of the end cap 90 are force fit, glued, or otherwise retained in the holes 88 of the proximal arm 87 of the outer cannula 40 as seen in FIG. 7. The proximal end 42 can optionally be provided with a side port (not shown) which can be manually operated to reduce and relieve pressure within the cavity 85. By relieving such pressure, blood within the cavity can be removed and the field of view can thereby be improved.

Figure 1C:
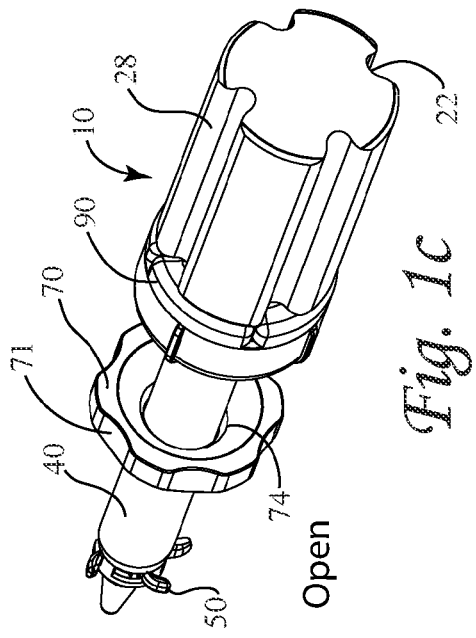
FIG. 1c is a rear perspective view of the surgical retention port of FIG. 1a in an open position.
Figure 1D:
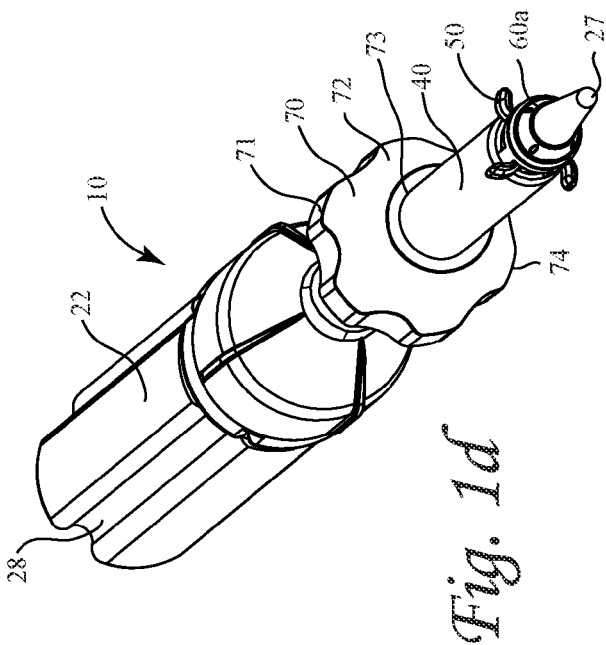
FIG. 1d is a front perspective view of the surgical retention port of FIG. 1a in an open position.

As seen in FIGS. 1b and 4a, the end cap 90 is preferably provided with visible indicators 95 on its proximal surface near its circumference. When the pointed instrument assembly 20 is aligned with the inner cannula 30 such that the fingers 50 are in a collapsed position, the grooves 28 on the handle 22 are located such that indicators 95 can be seen by the practitioner. When the handle 22 is rotated in order to cause the inner cannula 30 to rotate and to cause the fingers 50 to open, the grooves 28 on the handle 22 are rotated such that the view of the indicators 95 is obstructed (FIGS. 1c and 4b). Thus, the practitioner can determine that the fingers 50 are at least partially extended.

As seen best in FIG. 5, the proximal side of the end cap 90 defines a tapered entry or port 97. The tapered entry is useful for directing arthroscopic tools past the valves 84 and 82 and into and through the inner cannula 30 during use of the surgical retention port 10, as will be described hereinafter.

According to one embodiment of the invention, the surgical retention port 10 is provided with a locking collar 70. As seen in FIGS. 1a-1d, 2a, 2b, 5 and 6, the locking collar 70 has a proximal scalloped portion 71 which is designed for being gripped and rotated easily by a practitioner, and a tapered distally extending nose portion 72 which terminates in a flat ring 73. Ring 73 defines an oval-shaped opening 74. The oval-shaped opening 74 is similarly shaped to and slightly larger than the previously described oval-shaped outer surface of the elongate portion 41 of the outer cannula 40. In this manner, when the larger diameter opening of the ring 73 is aligned with the larger diameter outer surface of the elongate portion 41 of the outer cannula, the locking collar 70 can be easily slid forward and backward along the said outer cannula 40. When it is desired to lock the locking collar in place on the outer cannula, the locking collar 70 can be rotated to cause misalignment of the larger diameter axes (i.e., the smaller diameter opening of the ring 73 will be rotated toward the larger diameter outer surface of the elongate portion 41 of cannula 40) such that the locking collar 70 will engage and interfere with the cannula 40 (seen schematically in FIGS. 5 and 6), and lock into place. Rotation back will release the locking collar 70 from the cannula 40. Preferably, the diameter of the ring 72 is similar to the diameter of the instrument 10 defined by the open fingers 50 from tip 57 to tip 57. In this manner, when the fingers 50 are opened inside a patient's skin (e.g., adjacent a shoulder) and the locking collar 70 is slid down the cannula to engage the outside of the patient's skin, a strong and stable situation is established with the surgical retention port 10 affixed in the patient. That is, when the locking collar is locked on the cannula, it provides both longitudinal stability of the cannula within the patient and provides pressure on the outside of the outer cannula to cause sufficient interface between the inner and outer cannulas resulting in locking of the fingers in the open configuration. When the long pointed instrument assembly 20 is withdrawn from the inner cannula 30, slit valve 82 closes to prevent fluid from exiting the surgical sight via the retention trocar port. A port for arthroscopic (or laparoscopic) tools (not shown) is thus established.

In use, the surgical retention port 10 with the long pointed instrument 20, an inner cannula 30, an outer cannula assembly 40, rotatable fingers 50a-50d in a collapsed position, and locking collar 70 is obtained. The retention trocar port 10 can be pushed into an incision (not shown) of a patient such that the tapered distal end 26 of the instrument 20, and then the tapered distal end 35 of the inner cannula 30 (which extends past the distal end of the outer cannula 40—see FIG. 5), and then the tapered distal end 43 of the outer cannula 40 dilate the incision so that at least the distal ends of the inner and outer cannulas 30, 40 and fingers 50 are located inside the patient. By holding the proximal housing 42 of the outer cannula 40 and the handle 22 of the long pointed instrument, and rotating one relative to the other (e.g., rotating the handle 22 counterclockwise relative to the outer cannula 40), the fingers 50 coupled to the inner cannula 30 can be pushed into an extended position (FIG. 3b). With the fingers 50 in the extended position, the locking collar (if available) can be slid distally along the outer cannula until it engages the skin of the patient, and then rotated to lock into place. The long pointed instrument 20 can then be removed from the inner cannula and out through valves 82, 84 housed in the proximal housing of the outer cannula 40. Optionally, the long pointed instrument 20 can be removed before the locking collar 70 is slid distally or before it is rotated to lock into place.

With the long pointed instrument 20 removed from the assembly, the double slit valve 82 acts to prevent fluid from escaping through the retention trocar port 10. When desired, arthroscopic or laparoscopic instruments (not shown) can be inserted via the port 97 of the end cap 90, and past the washer valve 84 and double slit valve 82 and through the inner cannula 30 and out the distal end thereof to the surgical site (not shown). Upon completion of the surgery, or upon desiring to remove the arthroscopic or laparoscopic instrument for any reason, the arthroscopic or laparoscopic instrument may be withdrawn back through the proximal end of the retention trocar port 10, with the double slit valve 82 again acting to prevent fluid from exiting. The pointed instrument 20 is then reinserted into the inner cannula 30 via port 97, washer valve 84 and slit valve 82 until the handle 22 stops against the end cap 90. The locking collar 70 (if used) can then be rotated to unlock it from the outer cannula 40 and slid proximally out of engagement with the skin. With the pointed instrument 20 in place in the inner cannula 30, the handle 22 is rotated clockwise to cause the inner cannula 30 to rotate clockwise and to force fingers 50 to close into the collapsed position (FIG. 3a). The entire retention trocar port assembly 10 may then be removed from the surgical site.

A second embodiment of the invention is seen in FIGS. 8-10. The parts of the second embodiment which are the same or similar to the parts of the first embodiment are numbered with like numbers, except "100" higher.

The surgical retention port 110 of FIGS. 8-10 broadly includes a long pointed instrument (trocar or obturator) assembly 120, an inner cannula 130, an outer cannula assembly 140, rotatable fingers 150a-50d which are coupled by pins 160a-160d to the inner cannula 130, and an optional locking collar 170. The long pointed instrument assembly 120 includes a proximal handle 122, a shaft 124 defining a longitudinal axis x and having a rib, key or interface mechanism 125 for rotating the inner cannula 130 and a pointed distal tip 126. The proximal handle 122 is different than handle 22 of the first embodiment and has discs 122a coupled by fins 122b. The discs are spaced so as to permit the fingers of the practitioner to easily grip and rotate the handle 122.

The hollow inner cannula 130 extends about the long pointed instrument 120 in a manner which permits the long pointed instrument 120 to be movable longitudinally relative to said inner cannula 130. Thus, by gripping the handle 122 and moving it distally and proximally, the shaft 124 of the long pointed instrument 120 can be inserted into and through the cannula 130 and can be removed completely from the inner cannula 130. The inner cannula 130 has at or near its proximal end 131 at least one groove, slot or keyway (i.e., a second interface mechanism) 132 which is designed to receive the rib or key interface 125 of the shaft 124 of the long pointed instrument 20. In this manner, rotation of the long pointed instrument 120 about the long axis x causes rotation of the hollow inner cannula 130. In addition, the inner cannula 130 has a distal end 133 which defines four longitudinal holes 134a-134d (one shown in FIG. 8) which receive pins 160a-160d. The very distal end of said hollow inner cannula comprises a tapered distal ring 135 coupled to a more proximal portion 136 of the distal end 133 of the hollow inner cannula 130 by a plurality of links 137.

Unlike the links 37 of the first embodiment, links 137 of the second embodiment are essentially bars having a thickness substantially equal to the thickness of the hollow inner cannula 30 and do not include radially extending portions having a thickness less than the thickness of the hollow inner cannula 130. The links 137 define a plurality of gaps 138 in which at least a portion of the fingers 150 are located. The pins 160a-160d extend from the longitudinal holes 134a-134d in the distal ring 135 through the gaps 138 (and fingers 150) and into the holes 134a-134d in the more proximal portion 136 of the distal end of cannula 130. Proximal of the distal end 133 of the inner cannula 130 and distal the proximal end 131, the inner cannula 130 has at least one groove 139 in its outer surface for receiving an o-ring 180. The o-ring(s) seat(s) in the groove 139 and serve(s) the primary function of preventing fluid from exiting the surgical site through any gaps between the cannulas 130 and 140.

Another difference between inner cannula 130 and the inner cannula 30 of the first embodiment is that inner cannula 130 defines a locking slot 196 which is best seen in FIGS. 9b, 9c, and 10a. Locking slot 196 is cut into (but preferably not through) the inner cannula 130, is located distal the keyways 132, and is arranged as a bayonet lock with two narrowing areas 197a, 197b, through which a pin 149 of the outer cannula (discussed below) can be forced. In this manner, the pin 149 can assume three different positions within the locking slot 196 (e.g., 198a, 198b, 198c) and prevent inadvertent rotation of the inner cannula 130 relative to the outer cannula 140. When the pin 149 is in the position 198a shown in FIGS. 9b and 10a, the fingers 150 are in a collapsed position. When the inner cannula 130 is rotated counterclockwise relative to the outer cannula 140 such that pin 149 is forced through the first narrowing area 197a, the fingers 150 assume a partially open position (not shown). When the inner cannula 130 is further rotated counterclockwise relative to the outer cannula 140 such that pin 149 is forced through the second narrowing area 197b into position 198c, the fingers 150 assume a completely open position as shown in FIG. 9c. Alternatively the pin can be fixed relative to the inner cannula and forced through a locking slot in the outer cannula and to provide the same locking functionality.

Outer cannula 140 of the second embodiment includes an elongate portion 141, a proximal end 142 which houses a valve assembly 180, and a distal end 143. The outer cannula 140 is substantially identical to the outer cannula 40 of the first embodiment except that it includes the previously mentioned press fit pin 149 extending inwardly from the elongate portion 141 and located adjacent the locking slot 196 of the inner cannula 130. At least a part of the elongate portion 141 of the cannula has a slightly oval outer cross-section. The distal end 143 of the outer cannula 140 includes a tapered ring 144 coupled to the remainder of the distal end by a plurality of longitudinal bars 145 which define windows 146. The bars have two lateral faces 147, 148 which act as camming surfaces for the fingers 150 such that rotation of the inner cannula 130 in a first rotational direction relative to said outer cannula 140 causes the fingers to engage one face (e.g., 147), and rotation of the inner cannula in the opposite direction causes the fingers to engage the other face (e.g., 148).

Fingers 150a-150d are coupled to the inner cannula 130 by pins 160a-160d. As seen best in FIG. 9a, each of the fingers 150a-150d has an integral pivot portion 152 which rotates about the pins and an extending portion 154 which extends radially outwardly in an "open" position. More particularly, in cross-section, each finger 150 takes the general form of a shoe footprint with the heel being the pivot portion 152, and the sole being the extending portion 154. The pivot portions 152 sit in the gap areas 138 of the distal end of the inner cannula 130, and the pivot portions 152 have a thickness or diameter substantially equal to the diameter of the inner cannula 130. In a closed or collapsed configuration, the extending portions 154 sit in the gap areas 138 of the inner cannula 130 as well as in the windows 146 of the outer cannula 140.

With the inner cannula 130, outer cannula 140, and fingers 150 arranged as described, it will be appreciated that with the fingers 150 in a collapsed configuration, upon rotation of the inner cannula 140 counterclockwise (looking distally), the inside surfaces 155 of the fingers 150 near their tips 157 will engage the camming surfaces or faces 148 of first bars 145 such that the faces 148 will force the fingers 150 to rotate about the pins 160 and extend radially outwardly. Eventually, the outside surfaces of the rotating portions 152 will engage the links 137 such that rotation cannot continue. In the opposite direction, from the fully open position, rotation of the inner cannula 140 in a clockwise direction will not cause the fingers 150 to start closing until the outer surfaces 156 of the extending portions 154 of the fingers are engaged by the camming surfaces 147 of second bars 145. Continued clockwise rotation eventually causes the complete closing of the fingers 150. Thus, for any given finger, one bar 145 of the outer cannula 140 causes the finger to open, while a second bar 145 which is located ninety degrees clockwise of the first bar causes the finger to close.

Rotation of the inner cannula 130 relative to the outer cannula 140 is obtained by engagement of a projection, rib, or key 125 on instrument 120 with a keyway 132 of the inner cannula 130 (see FIG. 10), and rotation of the elongate pointed instrument 120 relative to the outer cannula 140. The rotation is typically accomplished by a practitioner through gripping the handle 122 of the instrument 120 in one hand, and the proximal end 142 of the outer cannula 140 with the other hand and rotating one or the other.

The proximal end 142 of the outer cannula 140 provides a housing for a valve assembly 180 which includes a polymeric flexible cross slit valve 182 and a polymeric stretchable washer valve 184. The housing is substantially identical to housing of the first embodiment and provides holes (not shown) for receiving pins 189 of end cap 190 which are force fit, glued, or otherwise retained in the holes.

According to one embodiment of the invention, the surgical retention port 110 is optionally provided with a locking collar 170. As seen in FIGS. 8 and 9, locking collar 170 is different than locking collar 70 of the first embodiment. More particularly, locking collar 170 is generally frustoconical in shape and tapers down in diameter as it extends proximally. The locking collar 170 includes external ribs 171 which are designed for being gripped and rotated easily by a practitioner. As seen best in FIG. 8, the locking collar 170 also includes an internal ring 173 with radial fingers 175. The ring 173 defines an oval-shaped opening 174. The oval-shaped opening 174 is similarly shaped to and slightly larger than the oval-shaped outer surface of the elongate portion 141 of the outer cannula 140. In this manner, when the larger diameter opening of the ring 173 is aligned with the larger diameter outer surface of the elongate portion 141 of the outer cannula, the locking collar 170 can be easily slid forward and backward along the outer cannula 140. When it is desired to lock the locking collar in place on the outer cannula, the locking collar 170 can be rotated to cause misalignment of the larger diameter axes (i.e., the smaller diameter opening of the ring 173 will be rotated toward the larger diameter outer surface of the elongate portion 141 of cannula 140) such that the locking collar 170 will engage and interfere with the cannula 140 and lock into place. Rotation back will release the locking collar 170 from the cannula 140.

The surgical retention port 110 of the second embodiment is used in substantially the same manner as the surgical retention port 10 of the first embodiment. The primary difference between the two is that additional resistance to rotation of the inner cannula 130 relative to the outer cannula 140 (and thus the opening and closing of fingers 150) is generated by the bayonet locking mechanism; i.e., pin 149 and locking slot 196 with narrowing areas 197a, 197b. Thus, in the second embodiment, the system is actively locked by the bayonet locking system, whereas in the first embodiment the system is actively locked by operation of the locking collar 70.

According to another embodiment of the invention, a highly flexible elastomeric sleeve 200 seen in FIG. 11a can be slid over the distal end of the outer cannula 40, 140 of either of the embodiments of the invention. The ends 201, 202 of the elastomeric sleeve are preferably fixed to the outer cannula by gluing, welding, or any other desired technique. End 201 is preferably fixed distal of fingers 50, 150, while end 202 is preferably fixed proximal of fingers 50, 150. With elastomeric sleeve 200 fixed in place and extending over windows 46, 146 of the outer cannula, when the fingers 50, 150 are opened, the fingers 50, 150 will cause the elastomeric sleeve 200 to stretch and "tent" as shown in FIG. 11b. In this manner enhanced anchoring may be accomplished.

Figure 12A:
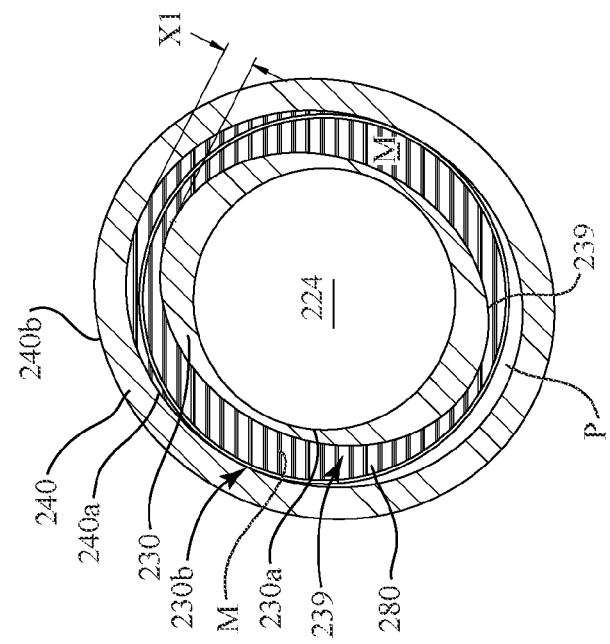
FIG. 12a is a cross-sectional view of another embodiment of the invention in a closed position.
Figure 12B:
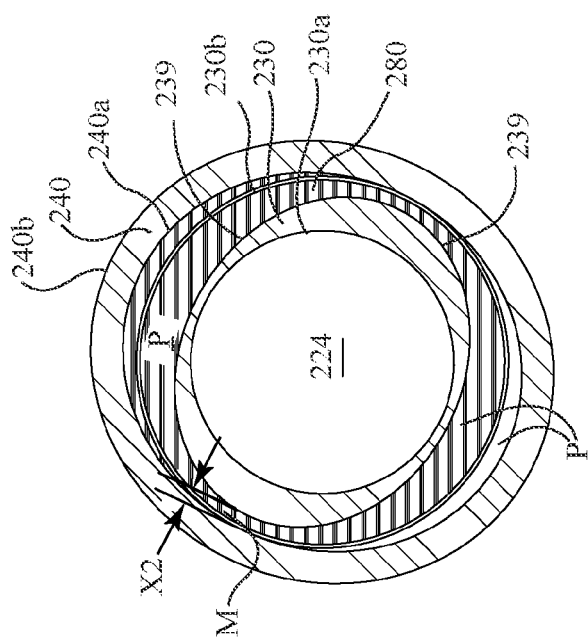
FIG. 12b is a cross-sectional view of the embodiment of FIG. 12a in an open position.

According to another embodiment of the invention, the inner cannula 30 (130) outer cannula 40 (140) and o-ring 80 may be adapted such that rotation of the inner cannula inside the outer cannula to open the fingers 50 (150) also provides significant friction which actively locks the unit in the open position. Significant force may be used to overcome the friction and move the fingers back into the closed position. More particularly, FIGS. 12a and 12b are cross-sections taken through a surgical retention port at the location of an o-ring (e.g., o-ring 80) described above with reference to FIG. 5. As in the previous embodiments, an obturator 224, an inner cannula 230, and an outer cannula 240 are shown. However, in the embodiment shown in FIGS. 12a and 12b the outer cannula 240 at the location of o-ring 280 has an inner surface 240a which is oval (as well as oval outer surface 240b), and the inner cannula 230 has an inner surface 230a which is circular and an outer surface 230b which is circular. As a result, at some points, the circular outer surface 230b of inner cannula 230 is contacting or nearly contacting the oval inner surface 240a of outer cannula 240, and at some points, there is gap between the two. In addition, the inner cannula 230 has a groove or race 239 which is oval in shape (the groove being between the oval inner line shown as 239 and the circular outer diameter 230b of the inner cannula 230). Thus, the groove 239 is deeper into the cannula 230 at some locations then at others. The o-ring 280 always fills the groove 239 as well as any space or gap between the outer surface 230b of the inner cannula 230 and the inner surface 240a of the outer cannula. With this arrangement, while the o-ring is squeezed or compressed in the groove 239 and between the outer surface 230b of the inner cannula 230 and the inner surface 240a of the outer cannula around the entire circumference of o-ring, the compression is relatively evenly distributed, with a maximum compression denoted in FIG. 12a by the minimum o-ring thickness X1. This result is obtained because the oval groove 239 is deepest where the space between the inner cannula and outer cannula is smallest (denoted by M), and the oval groove 239 is shallowest where the space between the inner cannula and outer cannula is largest (denoted by P) such that the o-ring stands significantly proud of the outer surface 230b of the inner cannula 230.

When the obturator 224 is rotated to cause the inner cannula 230 to rotate with respect to the outer cannula 240 (to open the fingers), the position of the o-ring 280 in the oval groove 239 reaches the situation shown in FIG. 12b. More particularly, as seen in FIG. 12b, the location on the inner cannula 230 where the groove 239 is deepest is now aligned with the location P where the space between the inner cannula 230 and the outer cannula 240 is largest, and the location on the inner cannula 230 where the groove 239 is shallowest is now aligned with the location where the space between the inner cannula 230 and outer cannula 240 is smallest (M). At this rotational configuration, the o-ring 280 is squeezed to a thickness X2 which is significantly smaller than X1 and the compression is not well distributed. The resulting forces tend to keep the inner cannula 230 locked relative to the outer cannula 240 with the fingers of the surgical retention port arranged in the open or extended position.

In the embodiment of FIGS. 12a and 12b, it desirable for the o-ring 280 to be able to be significantly compressed. The hardness chosen for the o-ring will generally depend upon the level of ovality of the groove 290 and the ovality of the inner surface 240a of the outer cannula 240. By way of example only, and not by way of limitation, o-ring 280 may be made from a material having a hardness of approximately 80A Durometer. It will be appreciated that the arrangement of FIGS. 12a and 12b can be used with either of the embodiments shown in FIGS. 1-7 and 8-10, with or without locking collar 70, 170, and with or without the bayonet lock arrangement of FIGS. 8-10.

There have been described and illustrated herein several embodiments of a surgical retention port and methods of its use. While particular embodiments of the invention have been described, it is not intended that the invention be limited thereto, as it is intended that the invention be as broad in scope as the art will allow and that the specification be read likewise. Thus, while the use of four fingers has been disclosed, it will be appreciated that different numbers of fingers could be used as well. Further, while the fingers are shown coupled to the cannula by a hinge constructed with a pivot pin, it is recognized that other pivot mechanisms including a living hinge construction integral with the cannula can be used. In addition, while a key and keyway engagement mechanism for the pointed instrument and inner cannula has been disclosed, it will be understood that other mechanisms can be used. It will therefore be appreciated by those skilled in the art that yet other modifications could be made to the provided invention without deviating from its spirit and scope as claimed.

What is claimed is:

1. A surgical retention port, comprising:
a long pointed instrument having a shaft defining a longitudinal axis, a distal tip capable of dilating an incision, a proximal handle, and an first interface mechanism;
a hollow inner cannula extending about said long pointed instrument with said long pointed instrument movable longitudinally relative to said inner cannula, said inner cannula having a distal end and a second interface mechanism, said second interface mechanism for engaging with said first interface mechanism of said long pointed instrument such that rotation of said long pointed instrument causes rotation of said hollow inner cannula;
a plurality of radially extendible fingers coupled to said distal end of said hollow inner cannula, each of said radially extendible fingers having a pivot portion and an extending portion and a pivot axis parallel said longitudinal axis; and
a hollow outer cannula having a proximal end, a distal end defining a periphery and a plurality of windows, said distal end including a plurality of bars between said windows, wherein
in a first configuration, said plurality of radially extendible fingers assume a collapsed arrangement with said extending portions at least partially contained within said plurality of windows and substantially within said periphery, and in a second configuration, said plurality of radially extendible fingers assume an opened configuration with said extending portions extending radially through said plurality of windows and beyond said periphery in a manner substantially perpendicular to said longitudinal axis.

2. A surgical retention port according to claim 1, wherein:
said distal end of said hollow inner cannula comprises a distal ring coupled to a more proximal portion of said hollow inner cannula by a plurality of links which define a plurality of gaps, and said surgical retention port further comprises a plurality of pins extending across said plurality of gaps from said distal ring to said more proximal portion, said plurality of pins extending through said pivot portions of said radially extendible fingers such that said radially extendible fingers rotate about pins.

3. A surgical retention port according to claim 2, wherein:
each of said links includes a portion having a thickness substantially equal to the thickness of said hollow inner cannula.

4. A surgical retention port according to claim 3, wherein:
each of said links includes a second radially extending portion having a thickness less than the thickness of said hollow inner cannula.

5. A surgical retention port according to claim 2, wherein:
said distal ring has a tapered thickness with a very distal end having a smaller outer diameter than a proximal end of said distal ring.

6. A surgical retention port according to claim 5, wherein:
said distal ring extends past said distal end of said outer cannula.

7. A surgical retention port according to claim 1, wherein:
said outer cannula has a shaft portion having an outer periphery defining an oval with a first outer diameter and a second outer diameter.

8. A surgical retention port according to claim 7, further comprising:

a locking collar extending about said shaft portion of said outer cannula, said locking collar defining an inner opening having an oval shape with a first inner diameter and a second inner diameter, said first inner diameter being greater than said first outer diameter and said second inner diameter being greater than said second outer diameter, and said second inner diameter being smaller than said first outer diameter.

9. A surgical retention port according to claim 1, wherein: each said extending portion of said fingers has a curved surface defined by a radius equal to the radius of the outer surface of said outer cannula.

10. A surgical retention port according to claim 1, wherein: said bars of said outer cannula include camming surfaces such that rotation of said inner cannula in a first rotational direction relative to said outer cannula causes said extending portions of said fingers to engage said camming surface and to cause said fingers to move from said first configuration toward said second configuration.

11. A surgical retention port according to claim 10, wherein:
in said second configuration said camming surfaces engage said pivot portions of said fingers.

12. A surgical retention port according to claim 11, wherein:
said bars of said outer cannula include second surfaces rotationally remote from said camming surfaces such that rotation of said inner cannula relative to said outer cannula in a second rotational direction opposite said first rotational direction said second surfaces to engage said extending portions of said fingers to cause said fingers to move from said second figuration toward said first configuration.

13. A surgical retention port according to claim 12, wherein:
for any particular finger, a camming surface of a first of said bars engages said particular finger to cause said finger to move from said first configuration toward said second configuration and a second surface of a second of said bars engages said particular finger to cause said finger to move from said second configuration toward said first configuration.

14. A surgical retention port according to claim 1, wherein:
said inner cannula defines a groove about its outer surface between said distal end of said inner cannula and said second interface mechanism, and said surgical retention port further comprises an O-ring located in said groove and contacting an inner surface of said outer cannula.

15. A surgical retention port according to claim 14, wherein:
adjacent said groove, said outer cannula has an oval inner surface and said inner cannula has a circular outer surface.

16. A surgical retention port according to claim 15, wherein:
said groove in said inner cannula is oval such that it is deeper in certain locations and shallower in other locations.

17. A surgical retention port according to claim 16, wherein:
said inner cannula and said outer cannula are rotationally arranged such that deeper locations of said groove are adjacent a smaller diameter of said oval inner surface of said outer cannula when said fingers assume said collapsed arrangement, and said shallower locations of said groove are adjacent said smaller diameter of said oval inner surface of said outer cannula when said fingers assume said open configuration.

18. A surgical retention port according to claim 1, wherein:
one of said first and second interface mechanisms is a longitudinally extending key and a second of said first and second interface mechanisms is a keyway slot.

19. A surgical retention port according to claim 1, further comprising:
an elastomeric sleeve fixed to the distal end of said outer cannula and extending freely over said plurality of windows.

20. A surgical retention port according to claim 1, wherein:
said outer cannula has an inwardly extending pin, and said inner cannula defines a locking slot having a plurality of predetermined locking positions for said extending pin.

21. A method, comprising:
a) obtaining a surgical retention port, comprising (i) a long pointed instrument having a shaft defining a longitudinal axis, a distal tip capable of dilating an incision, a proximal handle, and an first interface mechanism, (ii) a hollow inner cannula extending about said long pointed instrument with said long pointed instrument movable longitudinally relative to said inner cannula, said inner cannula having a distal end and a second interface mechanism, said second interface mechanism for engaging with said first interface mechanism of said long pointed instrument such that rotation of said long pointed instrument causes rotation of said hollow inner cannula, (iii) a plurality of radially extendible fingers coupled to said distal end of said hollow inner cannula, each of said radially extendible fingers having a pivot portion and an extending portion, and (iv) a hollow outer cannula having a proximal end, a distal end defining a periphery and a plurality of windows, said distal end including a plurality of bars between said windows, wherein in a first configuration, said plurality of radially extendible fingers assume a collapsed arrangement with said extending portions at least partially contained within said plurality of windows and substantially within said periphery, and in a second configuration, said plurality of radially extendible fingers assume an opened configuration with said extending portions extending radially through said plurality of windows and beyond said periphery in a manner substantially perpendicular to said longitudinal axis;
b) with said fingers in said collapsed arrangement, pushing said surgical retention port into an incision of a patient such that said distal end of said inner cannula, said distal end of said outer cannula, and said fingers are located inside the patient;
c) rotating said long pointed instrument and thereby said inner cannula relative to said outer cannula to force said fingers into said extended position;
d) removing said long pointed instrument from said inner cannula;
e) inserting a surgical instrument through said inner cannula and manipulating the surgical instrument;
f) removing the surgical instrument from said inner cannula;
g) reinserting said long pointed instrument into said inner cannula and rotating said long pointed instrument to force said fingers back into said collapsed arrangement; and
h) withdrawing said surgical retention port from the incision.

22. A method according to claim 21, wherein said surgical retention port further includes a locking collar, further comprising:
- after said rotating, sliding said locking collar over outer cannula until said locking collar engages the patient; and
- locking said locking collar in place by rotating said locking collar relative to said outer cannula.

23. A surgical retention port, comprising:
- a long pointed instrument having a shaft defining a longitudinal axis, a distal tip capable of dilating an incision, a proximal handle;
- a hollow inner cannula extending about said long pointed instrument with said long pointed instrument movable longitudinally relative to said inner cannula, said inner cannula having a distal end, said distal end of said hollow inner cannula comprises a distal ring coupled to a more proximal portion of said hollow inner cannula by a plurality of links which define a plurality of gaps, and a plurality of pins extending across said plurality of gaps from said distal ring to said more proximal portion;
- a plurality of radially extendible fingers coupled to said distal end of said hollow inner cannula, each of said radially extendible fingers having a pivot portion and an extending portion, said plurality of pins extending through said pivot portions of said radially extendible fingers such that said radially extendible fingers rotate about pins; and
- a hollow outer cannula having a proximal end, a distal end defining a periphery and a plurality of windows, said distal end including a plurality of bars between said windows, said hollow outer cannula and said hollow inner cannula being rotatably movable relative one to the other, wherein
- in a first configuration, said plurality of radially extendible fingers assume a collapsed arrangement with said extending portions at least partially contained within said plurality of windows and substantially within said periphery, and when said hollow inner cannula is rotated relative to said hollow outer cannula from said first configuration to a second configuration, said plurality of radially extendible fingers assume an opened configuration with said extending portions extending radially through said plurality of windows and beyond said periphery in a manner substantially perpendicular to said longitudinal axis.

24. A surgical retention port according to claim 23, wherein:
- each of said links includes a portion having a thickness substantially equal to the thickness of said hollow inner cannula.

25. A surgical retention port according to claim 24, wherein:
- each of said links includes a second radially extending portion having a thickness less than the thickness of said hollow inner cannula.

26. A surgical retention port according to claim 23, wherein:
- said distal ring has a tapered thickness with a very distal end having a smaller outer diameter than a proximal end of said distal ring.

27. A surgical retention port according to claim 26, wherein:
- said distal ring extends past said distal end of said outer cannula.

28. A surgical retention port according to claim 23, wherein:
- said outer cannula has a shaft portion having an outer periphery defining an oval with a first outer diameter and a second outer diameter, and said surgical retention port further comprises a locking collar extending about said shaft portion of said outer cannula, said locking collar defining an inner opening having an oval shape with a first inner diameter and a second inner diameter, said first inner diameter being greater than said first outer diameter and said second inner diameter being greater than said second outer diameter, and said second inner diameter being smaller than said first outer diameter.

29. A surgical retention port according to claim 23, wherein:
- each said extending portion of said fingers has a curved surface defined by a radius equal to the radius of the outer surface of said outer cannula.

30. A surgical retention port, comprising:
- a long pointed instrument having a shaft defining a longitudinal axis, a distal tip capable of dilating an incision, and a proximal handle;
- a hollow inner cannula extending about said long pointed instrument with said long pointed instrument movable longitudinally relative to said inner cannula, said inner cannula having a distal end;
- a plurality of radially extendible fingers coupled to said distal end of said hollow inner cannula, each of said radially extendible fingers having a pivot portion and an extending portion; and
- a hollow outer cannula having a proximal end, a distal end defining a periphery and a plurality of windows, said distal end including a plurality of bars between said windows, said bars of said outer cannula including camming surfaces, wherein
- in a first configuration said plurality of radially extendible fingers assume a collapsed arrangement with said extending portions at least partially contained within said plurality of windows and substantially within said periphery, and upon rotation of said inner cannula relative to said outer cannula in a first rotational direction, said camming surfaces cause said plurality of radially extendible fingers to move from said collapsed position to a second open configuration with said extending portions extending radially through said plurality of windows and beyond said periphery in a manner substantially perpendicular to said longitudinal axis.

31. A surgical retention port according to claim 30, wherein:
- in said second configuration said camming surfaces engage said pivot portions of said fingers.

32. A surgical retention port according to claim 31, wherein:
- said bars of said outer cannula include second surfaces rotationally remote from said camming surfaces such that rotation of said inner cannula relative to said outer cannula in a second rotational direction opposite said first rotational direction said second surfaces to engage said extending portions of said fingers to cause said fingers to move from said second figuration toward said first configuration.

33. A surgical retention port according to claim 32, wherein:
- for any particular finger, a camming surface of a first of said bars engages said particular finger to cause said finger to move from said first configuration toward said second configuration and a second surface of a second of said bars engages said particular finger to cause said finger to move from said second configuration toward said first configuration.

34. A surgical retention port according to claim 30, wherein:
said inner cannula defines a groove about its outer surface between said distal end of said inner cannula and said second interface mechanism, and said surgical retention port further comprises an O-ring located in said groove and contacting an inner surface of said outer cannula, adjacent said groove, said outer cannula has an oval inner surface and said inner cannula has a circular outer surface, and
said groove in said inner cannula is oval such that it is deeper in certain locations and shallower in other locations.

35. A method, comprising:
a) obtaining a surgical retention port, comprising (i) a long pointed instrument having a shaft defining a longitudinal axis, a distal tip capable of dilating an incision, and proximal handle, (ii) a hollow inner cannula extending about said long pointed instrument with said long pointed instrument movable longitudinally relative to said inner cannula, said inner cannula having a distal end; (iii) a plurality of radially extendible fingers coupled to said distal end of said hollow inner cannula, each of said radially extendible fingers having a pivot portion and an extending portion; and (iv) a hollow outer cannula having a proximal end, a distal end defining a periphery and a plurality of windows, said distal end including a plurality of bars between said windows, said bars of said outer cannula including camming surfaces, wherein in a first configuration said plurality of radially extendible fingers assume a collapsed arrangement with said extending portions at least partially contained within said plurality of windows and substantially within said periphery, and upon rotation of said inner cannula relative to said outer cannula in a first rotational direction, said camming surfaces cause said plurality of radially extendible fingers to move from said collapsed position to a second open configuration with said extending portions extending radially through said plurality of windows and beyond said periphery in a manner substantially perpendicular to said longitudinal axis;
b) with said fingers in said collapsed arrangement, pushing said surgical retention port into an incision of a patient such that said distal end of said inner cannula, said distal end of said outer cannula, and said fingers are located inside the patient;
c) rotating said inner cannula relative to said outer cannula in said first direction to force said fingers into said open configuration;
d) removing said long pointed instrument from said inner cannula;
e) inserting a surgical instrument through said inner cannula and manipulating the surgical instrument;
f) removing the surgical instrument from said inner cannula;
g) rotating said inner cannula relative to said outer cannula in a second direction opposite said first direction to force said fingers back into said collapsed arrangement; and
h) withdrawing said surgical retention port from the incision.

36. A method according to claim 35, wherein said surgical retention port further includes a locking collar, further comprising:
after said rotating, sliding said locking collar over outer cannula until said locking collar engages the patient; and
locking said locking collar in place by rotating said locking collar relative to said outer cannula.

37. A method, comprising:
a) obtaining a surgical retention port, comprising (i) a long pointed instrument having a shaft defining a longitudinal axis, a distal tip capable of dilating an incision, and proximal handle, (ii) a hollow inner cannula extending about said long pointed instrument with said long pointed instrument movable longitudinally relative to said inner cannula, said inner cannula having a distal end, said distal end of said hollow inner cannula comprises a distal ring coupled to a more proximal portion of said hollow inner cannula by a plurality of links which define a plurality of gaps, and a plurality of pins extending across said plurality of gaps from said distal ring to said more proximal portion (iii) a plurality of radially extendible fingers coupled to said distal end of said hollow inner cannula, each of said radially extendible fingers having a pivot portion and an extending portion, said plurality of pins extending through said pivot portions of said radially extendible fingers such that said radially extendible fingers rotate about pins, and (iv) a hollow outer cannula having a proximal end, a distal end defining a periphery and a plurality of windows, said distal end including a plurality of bars between said windows, wherein in a first configuration, said plurality of radially extendible fingers assume a collapsed arrangement with said extending portions at least partially contained within said plurality of windows and substantially within said periphery, and in a second configuration, said plurality of radially extendible fingers assume an opened configuration with said extending portions extending radially through said plurality of windows and beyond said periphery in a manner substantially perpendicular to said longitudinal axis;
b) with said fingers in said collapsed arrangement, pushing said surgical retention port into an incision of a patient such that said distal end of said inner cannula, said distal end of said outer cannula, and said fingers are located inside the patient;
c) rotating said inner cannula relative to said outer cannula in a first direction to force said fingers into said extended position;
d) removing said long pointed instrument from said inner cannula;
e) inserting a surgical instrument through said inner cannula and manipulating the surgical instrument;
f) removing the surgical instrument from said inner cannula;
g) rotating said inner cannula relative to said outer cannula in a second direction opposite said first direction to force said fingers back into said collapsed arrangement; and
h) withdrawing said surgical retention port from the incision.

38. A method according to claim 37, wherein said surgical retention port further includes a locking collar, further comprising:
after said rotating, sliding said locking collar over outer cannula until said locking collar engages the patient; and
locking said locking collar in place by rotating said locking collar relative to said outer cannula.

* * * * *